United States Patent [19]

Stephen

[11] 4,045,404
[45] Aug. 30, 1977

[54] HINDERED PHENOLIC NORBORNANE-2,3-DICARBOXIMIDES AND STABILIZED COMPOSITIONS

[75] Inventor: John F. Stephen, New City, N.Y.

[73] Assignee: Ciba-Geigy Corporation, Ardsley, N.Y.

[21] Appl. No.: 575,670

[22] Filed: May 8, 1975

Related U.S. Application Data

[62] Division of Ser. No. 429,234, Dec. 28, 1973, Pat. No. 3,896,147.

[51] Int. Cl.² ............................ C08K 5/00; C08L 4/00
[52] U.S. Cl. .......................... 260/45.8 N; 260/3.26 R; 260/45.85 S
[58] Field of Search ................ 260/45.8 N, 3.26 R, 260/45.85 S

[56] References Cited

U.S. PATENT DOCUMENTS 3,234,233  3/1966  Bolger .................................. 260/326

Primary Examiner—Melvin I. Marquis
Assistant Examiner—William Parker
Attorney, Agent, or Firm—Nestor W. Shust

[57] ABSTRACT

Compounds having the formula

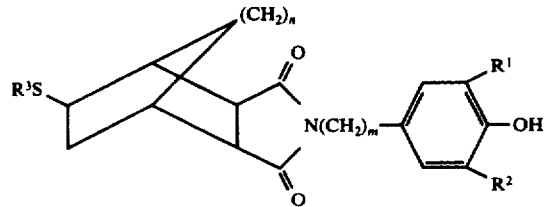

wherein $R^1$ and $R^2$ are lower alkyl, $R^3$ is alkyl, another hindered phenolic norbornane-2,3-dicarboximide group, or a group —$(CH_2)$—$CO_2R^4$ and $m$ is 0 to 3, $n$ is 1 or 2 and $R^4$ is alkyl, are good oxidative and thermal stabilizers of synthetic polymers.

6 Claims, No Drawings

HINDERED PHENOLIC NORBORNANE-2,3-DICARBOXIMIDES AND STABILIZED COMPOSITIONS

This is a divisional of application Ser. No. 429,234, filed on Dec. 28, 1973, now U.S. Pat. No. 3,896,147.

DETAILED DISCLOSURE

This invention relates to hindered phenolic norbornane-2,3-dicarboximides and organic compositions stabilized therewith. More specifically, these compounds are useful as stabilizers of organic materials which are subject to oxidative and thermal degradation. The compounds of this invention can be represented by the formula

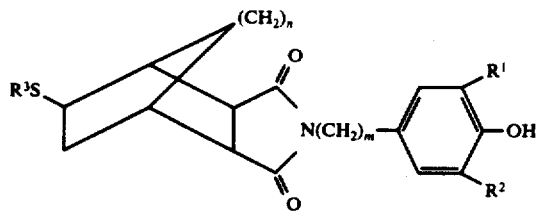

I wherein
$R^1$ and $R^2$ are the same or different (lower) alkyl groups of 1 to 4 carbon atoms,
$m$ has a value of 0 to 3,
$n$ has a value of 1 or 2, and
$R^3$ is alkyl group of 1 to 18 carbons, a group of the formulae

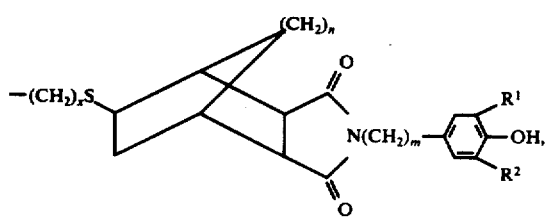

II

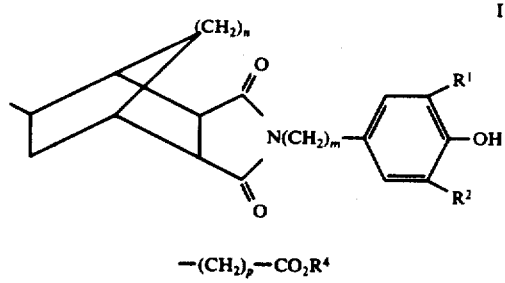

III or $$-(CH_2)_p-CO_2R^4$$

IV where
$x$ has a value of 2 to 18,
$R^4$ is alkyl group of 1 to 18 and
$p$ has a value of 1 or 2.

The $R^1$ and $R^2$ groups can be any straight or branched chain alkyl having 1 to 4 carbon atoms, such as methyl, ethyl, isopropyl, n-butyl and tert-butyl. Preferably these groups are methyl, isopropyl and tert-butyl groups. Most preferably both groups are tert-butyl. The integer $n$ is preferably 1.

The $R^3$ group can be any alkyl, that is, methyl, ethyl, propyl, butyl, hexyl, octyl and the like up to 18 carbons, but preferably it is from 4 to 18 carbons. In the preferred embodiment $R^3$ can be also a group of formulae II, III and IV where $R^1$ and $R^2$ are preferably methyl, isopropyl or tert-butyl and especially tert-butyl and $x$ has a value of 2 to 18 and especially 2 to 6. $R^3$ can also be preferably a group $-(CH_2)_p-CO_2R^4$ where $R^4$ is alkyl from 4 to 18 carbons.

The compounds of formula I wherein $m$ is 0, 2 and 3 can be prepared by reacting the appropriate 3,5-dialkyl-4-hydroxyphenyl substituted amine of the formula

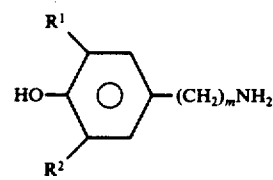

V wherein $R^1$ and $R^2$ are as defined previously, with the appropriate exo-5-alkylthionorbornane-endo-2,3-dicarboxylic anhydride in a suitable solvent such as toluene at reflux temperatures. Exo-5-alkylthionorbornane-endo-2,3-dicarboxylic anhydrides can be prepared from 5-norbornene-endo-2,3-dicarboxylic anhydride and an appropriate mercaptan in the presence of a suitable initiator such as azobisisobutyronitrile in a solvent such as dioxane. 5-Norbornene-endo-2,3-dicarboxylic anhydride is commercially available.

The 3,5-dialkyl-4-hydroxyphenylsubstituted amines wherein $m$ is 0 can be prepared as described in U.S. Pat. No. 3,198,797. The amine, when $m$ is 2 can be prepared, for example, through chloromethylation of a dialkylphenol as described in U.S. Pat. No. 2,838,571, followed by treatment of the resulting chloromethyl derivative with sodium or potassium cyanide and reduction of the resultant dialkyl-hydroxyphenylacetonitrile to the amine. The amine wherein $m$ is 3 can be prepared by reducing the appropriate 3-(3,5-dialkyl-4-hydroxyphenyl)-propionitrile with lithium aluminum hydride to yield the corresponding amine. The nitrile can be prepared according to the method described in U.S. Pat. No. 3,121,732 wherein the appropriate dialkylphenol is reacted with acrylonitrile.

The compounds of the formula I wherein $m$ is 0, 2 and 3 can also be prepared by free radical addition of an appropriate mercaptan of an imide of the formula

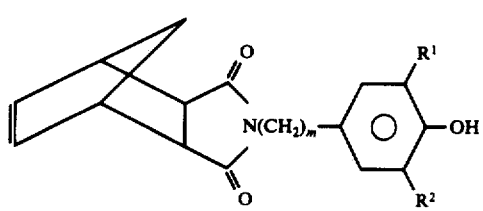

VI wherein $R^1$, $R^2$ and $m$ are as defined previously, in the presence of a suitable initiator such as azobisisobutyronitrile in a solvent such as dioxane.

The preparation of imides of the formula VI is described in our copending application (GC 666). The Compounds of formula I wherein $m$ is 1 can be prepared by reacting the appropriate 3,5-dialkyl-4-hydroxybenzyl-dialkyl amine of the formula

VII

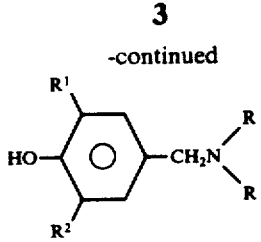

wherein $R^1$ and $R^2$ are as defined previously and R is an alkyl group such as methyl or ethyl, with the appropriate exo-5-alkylthionorbornane-endo-2,3-dicarboximide in a suitable solvent such as N,N-dimethylformamide. The 3,5-dialkyl-4-hydroxybenzyl-dialkyl amines can be prepared as described by E. P. Previc et al., Industrial and Engineering Chemistry, 53, 469 (1961).

Exo-5-alkylthionorbornane-endo-2,3-dicarboximides can be prepared by free radical addition of the appropriate mercaptan to 5-norbornene-endo-2,3-dicarboximide in the presence of an initiator such as azobisisobutyronitrile and a solvent such as dioxane.

5-Norbornene-endo-2,3-dicarboximide can be prepared from 5-norbornene-endo-2,3-dicarboxylic anhydride by the procedure described by W. S. Worrall in J. Amer. Chem. Soc. 82, 5707 (1960).

The compounds of formula I wherein $m$ is 1 and $R^3$ is $(CH_2)_pCO_2R^4$ can also be prepared by esterifying the appropriate N-(3,5-di-tert-butyl-4-hydroxybenzyl)-exo-5-(2-carboxyethylthio)-norbornane-endo-2,3-dicarboximide and N-(3,5-di-tert-butyl-4-hydroxybenzyl)-exo-5-carboxymethylthionorbornane-endo-2,3dicarboximide with an alcohol in the presence of a suitable catalyst such as p-toluenesulfonic acid. The above acids can be prepared by hydroxybenzylating the corresponding exo-5-(2-carboxyethylthio)-norbornane-endo-2,3-dicarboximide and exo-5-carboxymethylthionorbornane-endo-2,3-dicarboximide with the appropriate 3,5-dialkyl-4-hydroxybenzyldialkyl amine of the formula IV. Exo-5-(2-carboxyethylthio)-norbornane-endo-2,3-dicarboximide and exo-5-carboxymethylthionorbornane-endo-2,3-dicarboximide can be prepared by free radical addition of 3-mercaptopropionic and mercaptoacetic acid, respectively, to 5-norbornene-endo-2,3-dicarboximide in the presence of an initiator such as azobisisobutyronitrile in a solvent such as dioxane.

The following examples further illustrate the preparation of the compounds without introducing any limitations.

EXAMPLE 1

Exo-5-(2-carboxyethylthio)-norbornane-endo-2,3-dicarboximide

In a nitrogen atmosphere, 3-mercaptopropionic acid (11.7 g, 0.11 mole) was added to a stirred solution of 5-norbornene-endo-2,3-dicarboximide (16.3, 0.1 mole) in 100 ml of dioxane. The temperature rose from 25° to 38°. The mixture was then heated at 65°-70° and a solution of azobisisobutyronitrile (1.6 g) in 40 ml of dioxane was added over a period of 1.5 hours. After the addition was completed the mixture was heated at 65°-70° for 20 hours. The dioxane was evaporated under reduced pressure and the residue thus obtained was recrystallized from ethanol to give 17.4 g (65%) of the title compound, m.p. 187°-189°.

EXAMPLE 2

N-(3,5-di-tert-butyl-4-hydroxybenzyl)-exo-5-(2-carboxyethylthio)-norbornane-endo-2,3-dicarboximide In a nitrogen atmosphere, a stirred-mixture of the above imide (16.2 g. 0.06 mole) and 2,6-di-t-butyl-4-dimethyl-aminomethylphenol (17.4 g, 0.666 mole) in 100 ml of N,N-dimethylformamide was heated at 110°-120° for 21 hours. The mixture was poured into water and the oily product was extracted with ether. The ether extract was washed with dilute hydrochloric acid and water. After drying over $Na_2SO_4$ the ether solution was evaporated to yield a solid residue. After trituration with petroleum ether the solid of 21.0 g was recrystallized from ethanol-water to give 19.1 g (65%) of hydroxybenzylated imide, m.p. 164°-166°.

EXAMPLE 3

N-(3,5-di-tert-butyl-4-hydroxybenzyl)-exo-5-(2-carbo-n-dodecyloxyethylthio)-norbornane-endo-2,3-dicarboximide A stirred mixture of the product of Example 2 (10.7 g, 0.0224 mole), dodecyl alcohol (4.1 g, 0.022 mole) and p-toluenesulfonic acid (100 mg.) in 75 ml of toluene was refluxed for 36 hours, water being removed with a Dean-Stark trap. The toluene was evaporated under reduced pressure, and the residual oil thus obtained was dissolved in ether. The ether solution was washed with aqueous sodium carbonate and water. Evaporation of the dried ($Na_2SO_4$) ether solution gave 11.5 g (88%) of the desired ester as an oil which was heated at 85°/0.05 mm for 12 hours prior to analysis:

Anal. Calcd. for $C_{39}H_{61}NO_5S$: C, 71.41; H, 9.37; N, 2.13; Found: C, 71.81; H, 9.42; N, 2.08.

EXAMPLE 4

Exo-5-n-Octadecylthionorbornane-endo-2,3-dicarboxylic anhydride

In a nitrogen atmosphere a stirred mixture of 5-norbornene-endo-2,3-dicarboxylic anhydride (16.3 g, 0.1 mole) and n-octadecyl mercaptan (30 g, 0.105 mole) in 100 ml of dioxane containing 0.2 g of azobisisobutyronitrile was heated at 70°-75° for 18 hours. Upon cooling, heptane was added and the precipitated solid was filtered off and was recrystallized from methanol to give 28.1 g (62.5%) of the title anhydride, m.p. 111°-113°.

EXAMPLE 5

N-(3,5-di-tert-butyl-4-hydroxyphenyl)-exo-5-n-octadecylthionorbornane-endo-2,3-dicarboximide Under nitrogen a solution of exo-5-n-octadecylthionorbornane-endo-2,3-dicarboxylic anhydride (11.3 g, 0.025 mole) and 2,6-di-tert-butyl-4-aminophenol (5.6 g, 0.025 mole) in 100 ml of xylene was refluxed for 6 hours, water being removed with a Dean-Stark trap. The xylene was evaporated under reduced pressure and the oily residue thus obtained was triturated with methanol whereupon it solidified. Recrystallization from ethanol-methanol mixture gave 7.0 g (43%) of the title imide, m.p. 67°-69°.

EXAMPLE 6 exo-5-n-Dodecylthionorbornane-endo-2,3-dicarboxylic anhydride

In a nitrogen atmosphere a stirred mixture of 5-norbornene-endo-2,3-dicarboxylic anhydride (24.6 g, 0.15 mole) and lauryl mercaptan (31.8 g, 0.157 mole) in 150 ml of dioxane containing 0.2 g of azobisisobutyronitrile was heated at 60°-70° for 20 hours. The solvent and excess mercaptan were evaporated under reduced pressure and the oily residue thus obtained was crystallized from petroleum ether to give 27.0 g (49.0%) of exo-5-n-dodecylthionorbornane-endo-2,3-dicarboxylic anhydride, m.p. 69°-71°.

EXAMPLE 7

N-(3,5-di-tert-butyl-4-hydroxyphenethyl)-exo-5-n-dodecylthionorbornane-endo-2,3-dicarboximide Under nitrogen a stirred mixture of exo-5-n-dodecylthionorbornane-endo-2,3-dicarboxylic anhydride (9.16 g, 0.025 mole) and 3,5-di-tert-butyl-4-hydroxyphenethyl amine (6.23 g, 0.025 mole) in 100 ml of dry toluene was heated at 80°-85° for 1 hour in a flask equipped with a Dean-Stark trap. p-Toluenesulfonic acid (0.05 g) was added and the mixture was heated under reflux for 5 hours. The toluene was evaporated under reduced pressure and the residue was triturated with petroleum ether to give a solid product of 12.2 g. Recrystallization from methanol gave 8.6 g (58%) of the desired imide, m.p. 72°-75°.

EXAMPLE 8

N-(3,5-di-tert-butyl-4-hydroxyphenylpropyl)-exo-5-n-dodecylthionorbornane-endo-2,3-dicarboximide In a nitrogen atmosphere a stirred solution of exo-5-n-dodecylthionorbornane-endo-2,3-dicarboxylic anhydride (9.16 g, 0.025 mole) and 3,5-di-tert-butyl-4-hydroxyphenylpropyl amine (6.58 g, 0.025 mole) in 100 ml toluene was heated at 80°-85° for 1 hour. p-Toluenesulfonic acid (0.05 g) was added and the mixture was heated under reflux for 5 hours, water being removed with a Dean-Stark trap. The toluene was evaporated in vacuo to give 12.5 g of a solid residue. Recrystallization from methanol gave 10.9 g (71%) of the title imide, m.p. 82°-84°.

EXAMPLE 9

N-(3,5-di-tert-butyl-4-hydroxyphenyl)-exo-5-n-dodecylthionorbornane-endo-2,3-dicarboximide In a nitrogen atmosphere a stirred solution of N-(3,5-di-tert-butyl-4-hydroxyphenyl)-5-norbornene-endo-2,3-dicarboximide (3.61 g, 0.098 mole) and lauryl mercaptan (21.3 g, 0.105 mole) in 100 ml of dioxane containing azobisisobutyronitrile (1.6 g, 0.01 mole) was heated at 75°-80° for 3 hours. The dioxane was evaporated under reduced pressure and the resulting oil was crystallized twice from aqueous methanol to give 28.0 g (50.0%) of N-(3,5-di-tert-butyl-4-hydroxyphenyl)-exo-5-n-dodecylthionorbornane-endo-2,3-dicarboximide, m.p. 68°-70°.

EXAMPLE 10 exo-5-n-Dodecylthionorbornane-endo-2,3-dicarboximide

In a nitrogen atmosphere a stirred mixture of 5-norbornene-endo-2,3-dicarboximide (24.6 g, 0.15 mole) and lauryl mercaptan (33.3 g, 0.165 mole) in 150 ml of dioxane was heated to 65° when a solution of azobisisobutyronitrile (0.25 g) in 5 ml of dioxane was added. The mixture was then heated at 65° for ~ 18 hours. The dioxane was evaporated in vacuo and the residue was recrystallized from heptane and then methanol to give 33.0 g (60%) of exo-5-n-dodecylthionorbornane-endo-2,3-dicarboximide, m.p. 113°-115°.

EXAMPLE 11

N-(3,5-di-tert-butyl-4-hydroxybenzyl)-exo-5-n-dodecylthionorbornane-endo-2,3-dicarboximide In a nitrogen atmosphere, a stirred mixture of exo-5-n-dodecylthionorbornane-endo-2,3-dicarboximide (10.8 g, 0.03 mole) and 2,6-di-tert-butyl-4-dimethylaminomethylphenol (8.3 g, 0.0315 mole) in 100 ml of N,N-dimethylformamide was heated at 120°-125° for 4 hours. The cold mixture was poured into water and the oil which separated was extracted with ether. The ether extract was washed with dilute hydrochloric acid and then water. The dried ($Na_2SO_4$) solution was evaporated under reduced pressure to give 15.8 g of a viscous oil. Chromatography over silica gel using heptane as solvent gave 7.6 g of pure title compound as a viscous oil.

Anal. Calcd. for $C_{36}H_{57}NO_3S$: C, 74.05; H, 9.84; N, 2.40; Found: C, 74.33; H, 9.92; N, 2.35.

Following the above procedure except-for employing 2,6-dimethyl-4-dimethylaminomethyl there is obtained N-(3,5-dimethyl-4-hydroxyphenyl)-exo-5-(2-carbo-n-dodecyloxyethylthio)-norbornane-endo-2,3-dicarboximide.

EXAMPLE 12 exo-5-(2-carbo-n-dodecyloxyethylthio)-norbornane-endo-2,3-dicarboxylic anhydride In a nitrogen atmosphere a stirred mixture of 5-norbornene-endo-2,3-dicarboxylic anhydride (16.4 g, 0.1 mole) and n-dodecyl-3-mercaptopropionate (29.4 g, 0.105 mole) in 150 ml of dioxane containing 0.2 g of azobisisobutyronitrile was heated at 65°-70° for 18 hours. The dioxane was evaporated under reduced pressure to give an oily residue which was dissolved in hexane. The hexane solution was filtered to remove insoluble material and the filtrate was evaporated to give 43.0 g (98%) of the desired anhydride, m.p. 44°-47°.

EXAMPLE 13

N-(3,5-di-tert-butyl-4-hydroxyphenyl)-exo-5-(2-carbo-n-dodecyloxyethylthio)-norbornane-endo-2,3-dicarboximide Under nitrogen, a stirred solution of the above anhydride (11.0 g, 0.025 mole) and 2,6-di-tert-butyl-4-aminophenol (5.55 g, 0.025 mole) in 150 ml of dry toluene was heated at 90° for 30 minutes and then under reflux for 5 hours, water being removed with a Dean-Stark trap. The toluene was evaporated under reduced pressure and the oily residue was purified by dry column chromatography on silica gel using chloroform as solvent. In this way there was obtained 4.8 g (30.0%) of pure esterimide as an oil.

Anal. Calcd. for $C_{38}H_{59}NO_5S$: C, 71.10; H, 9.27; N, 2.18; S, 4.99; Found: C, 71.40; H, 8.98; N, 2.25; S, 4.65.

Employing the above procedure except for employing 2,6-diisopropyl-4-aminophenol and 2-methyl-6-tert-butyl-4-aminophenol, there are obtained N-(3,5-diisopropyl-4-hydroxyphenyl)-exo-5-(2-carbo-n-dodecyloxyethylthio)-norbornane-endo-2,3-dicarboximide and N-(3-methyl-5-tert-butyl-4-hydroxyphenyl)-exo-5-(2-carbo-n-dodecyloxyethylthio)-norbornane-endo-2,3-dicarboximide.

Compounds reported in Table I were prepared according to the procedures described above.

TABLE I

| Ex. No. | R³ | m | m.p. |
|---|---|---|---|
| 14 | n-C₈H₁₇ | 0 | 77–79° C |
| 15 | n-C₈H₁₇ | 1 | oil* |
| 16 | n-C₁₈H₃₇ | 1 | oil* |
| 17 | —(CH₂)₃—S—Y** | 1 | 120–122° C |
| 18 | —Y** | 1 | 230–257° C |
| 19 | —(CH₂)₂—CO₂C₄H₉-n | 1 | oil* |
| 20 | —(CH₂)₂—CO₂C₁₈H₃₇-n | 1 | oil* |
| 21 | —CH₂CO₂C₁₂H₂₅-n | 1 | oil |
| 22 | —CH₂CO₂C₁₈H₃₇-n | 1 | oil* |

*Each compound that was an oil was purified by chromatography over silica gel. The microanalytical results for hydrogen, carbon and nitrogen corresponded to the calculated values.

**—Y has the structure

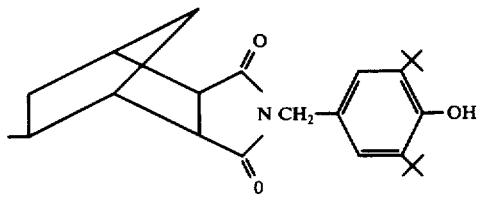

TABLE II

Light Stabilization of Polypropylene

| Stabilizer* | Time to 0.5 Carbonyl Absorbance Units |
|---|---|
| 1. 0.2% Compound of Ex. 9 | 1170 hours |
| 2. 0.2% Compound of Ex. 5 | 1105 hours |
| 3. 0.2% Compound of Ex. 11 | 1100 hours |
| 4. 0.2% Compound of Ex. 16 | 945 hours |
| 5. 0.2% Compound of Ex. 17 | 950 hours |
| 6. 0.2% Compound of Ex. 18 | 790 hours |
| 7. 0.2% Compound of Ex. 19 | 945 hours |
| 8. 0.2% Compound of Ex. 3 | 1090 hours |
| 9. 0.2% Compound of Ex. 20 | 795 hours |
| 10. 0.2% Compound of Ex. 13 | 790 hours |
| 11. 0.2% Compound of Ex. 21 | 730 hours |
| 12. 0.2% Compound of Ex. 22 | 740 hours |
| 13. No stabilizers | ~170 hours |

*The composition also contains 0.5% of UV absorber 2(2'-hydroxy-3',5'-di-tert-butylphenyl)-5-chlorobenzotriazole.

The compositions of Table II are equally stabilized when 2{2'-hydroxy-3',5'-di-t-butylphenyl}-5-chlorobenzotriazole is replaced with the following UV absorbers:

a. 2-hydroxy-4-methoxy-5-sulfobenzophenone trihydrate
b. 2-hydroxy-4-n-octoxybenzophenone
c. {2,2'-thiobis(4-t-octylphenolate)}-n-butylamine nickel II
d. p-octylphenyl salicylate
e. 2,2'-dihydroxy-4,4'-dimethoxybenzophenone
f. 2{2'-hydroxy-5'-methylphenyl}-benzotriazole Other hindered phenolic antioxidants may be used in place of di-octadecyl(3,5-di-t-butyl-4-hydroxybenzyl)-phosphate in the above mentioned compositions for example di-n-octadecyl α-(3-t-butyl-4-hydroxy-4-methylbenzyl)malonate, 2,4-bis(n-octylthio)-6-(3,5-di-t-butyl-4-hydroxyaniline)-1,3,5-triazine, octadecyl 3-(3',5'-di-t-butyl-4'-hydroxyphenyl)propionate, pentaethylthritol-tetrakis[3-(3,5-di-t-butyl-4-hydroxyphenyl)-propionate]tris-3,5-di-t-butyl-4-hydroxyphenyl-)isocyanurate, 2,6-di-tert-butyl-4-methylphenyl, N,N,N-tris-(3,5-di-tert-butyl-4-hydroxybenzyl-)isocyanurate, and 2,4,6-tris-(3,5-di-tert-butyl-4-hydroxybenzyl)-1,3,5-trimethylbenzyl.

EXAMPLE 15

Unstabilized polypropylene powder (Hercules Profax 6501) was thoroughly blended with the stabilizers indicated in Table III below. The blended materials were then milled on a two-roll mill at 182° C for 10 minutes, after which time the stabilized polypropylene was sheeted from the mill and allowed to cool.

The milled polypropylene sheets were then cut into pieces and pressed for 7 minutes on a hydraulic press at 218° C, 2,000 pounds per square inch pressure. The resulting plaques of 25 mil thickness were tested for resistance to accelerated aging in a forced draft oven at 150° C. When the plaques showed the first signs of decomposition (e.g., cracking or brown edges) they were considered to have failed. The results were as follows:

TABLE III

Oven Aging of Polpropylene

| | Time to Failure in Hours Formulations | | |
|---|---|---|---|
| Stabilizer | A¹ | B | C³ |
| 1. Compound of Ex. 9 | 260 | 270 | 305 |
| 2. Compound of Ex. 5 | 415 | 425 | 375 |
| 3. Compound of Ex. 11 | 280 | 265 | 530 |
| 4. Compound of Ex. 16 | 365- | 405 | 380 |
| 5. Compound of Ex. 17 | 270 | 190 | 950 |
| 6. Compound of Ex. 18 | 50 | 50 | 715 |
| 7. Compound of Ex. 19 | 65 | 65 | 185 |
| 8. Compound of Ex. 3 | 280 | 243 | 875- |
| 9. Compound of Ex. 20 | 200 | 170 | 420 |
| 10. Compound of Ex. 13 | 545 | 420 | 655 |
| 11. Compound of Ex. 21 | 450 | 425 | 545 |
| 12. Compound of Ex. 22 | 465 | 530 | 580 |
| 13. No stabilizer | ~3 | | |

¹Formulation A contains 0.2% of the indicated stabilizer of this invention.
²Formulation B contains 0.2% of the indicated stabilizer and 0.5% of UV absorber 2(2'-hydroxy-3',5'-di-tert-butylphenyl)-5-chlorobenzotriazole.
³Formulation C contains 0.1% of the indicated stabilizer and 0.3% of dilaurylthiodipropionate.

What is claimed is:

1. A composition of matter comprising an organic material normally subject to oxidative, thermal and/or ultraviolet light degradation and (a) from 0.01 to 5% of a stabilizer having the formula

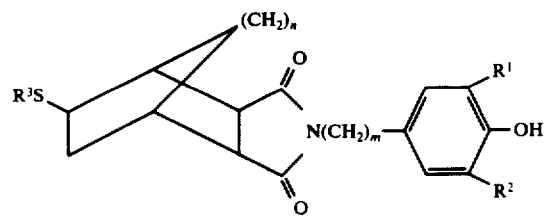

I wherein
R¹ and R² are the same or different (lower) alkyl groups of 1 to 4 carbon atoms,
m has a value of 0 to 3,
n has a value of 1 and 2, and
R³ is alkyl group of 1 to 18 carbons, a group of the formulae

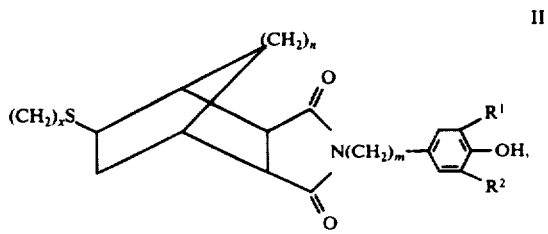

II

III or

-continued

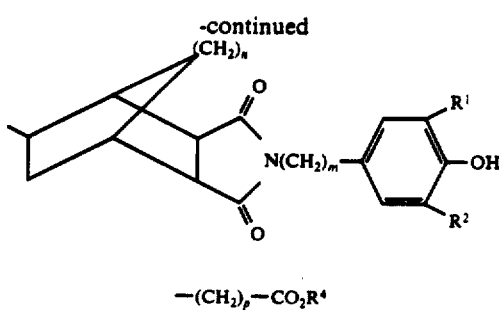

$-(CH_2)_p-CO_2R^4$     IV where $x$ has a value of 2 to 18, $R^4$ is alkyl of 1 to 18 carbons, and $p$ has a value of 1 or 2, b. from 0 to 5% of a UV absorber, and
c. from 0 to 5% of a co-stabilizer.

2. A composition of claim 1 wherein the organic matter is polyolefin.

3. A composition of claim 2 wherein $R^1$ and $R^2$ are methyl, isopropyl or tert-butyl, $n$ is 1, $R^3$ is alkyl from 4 to 18 carbons, or a group of formulae II, III or IV where $x$ is 2 to 4 and $R^4$ is alkyl having from 4 to 18 carbons.

4. A composition of claim 3 wherein the polyolefin is polypropylene.

5. A composition of claim 4 containing from 0.01 to 5% of UV absorber 2( 2'-hydroxy-3',5'-di-tert-butylphenyl)-5-chlorobenzotriazole.

6. A composition of claim 4 containing from 0.01 to 5% of co-stabilizer dilaurylthiodipropionate.

* * * * *